United States Patent
Willis

(10) Patent No.: US 7,179,224 B2
(45) Date of Patent: Feb. 20, 2007

(54) ORGAN MANIPULATOR AND POSITIONER AND METHODS OF USING THE SAME

(75) Inventor: Geoffrey H. Willis, Redwood City, CA (US)

(73) Assignee: Cardiothoracic Systems, Inc., Santa Clara, CA (US)

( * ) Notice: Subject to any disclaimer, the term of this patent is extended or adjusted under 35 U.S.C. 154(b) by 232 days.

(21) Appl. No.: 10/749,061

(22) Filed: Dec. 30, 2003

(65) Prior Publication Data

US 2005/0148822 A1    Jul. 7, 2005

(51) Int. Cl.
*A61B 1/32* (2006.01)
(52) U.S. Cl. .................. 600/205; 600/201; 600/210
(58) Field of Classification Search ............... 600/490, 600/37, 207, 210
See application file for complete search history.

(56) References Cited

U.S. PATENT DOCUMENTS

| 452,131 A | 5/1891 | Haughawout |
| 810,675 A | 1/1906 | Myers |
| 1,706,500 A | 3/1929 | Smith |
| 2,082,782 A | 6/1937 | Allen |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,361,133 A | 1/1968 | Kimberley et al. |
| 3,392,722 A | 7/1968 | Jorgensen |
| 3,466,079 A | 9/1969 | Mammel |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jacobs |

(Continued)

FOREIGN PATENT DOCUMENTS

DE    3138589 A1    4/1983

(Continued)

OTHER PUBLICATIONS

C.W. Akins et al., "Preservation of Interventricular Septal Function in Patients Having Coronary Artery Bypass Grafts Without Cardiopulmonary Bypass," American Heart Journal, vol. 107, No. 2 Feb. 1984, pp. 304-309.

(Continued)

*Primary Examiner*—Cris L Rodriuez
*Assistant Examiner*—Patrick J. Kilkenny
(74) *Attorney, Agent, or Firm*—Law Office of Alan W. Cannon

(57) ABSTRACT

Devices and methods are provided for manipulating and supporting an organ. The subject devices are characterized by having an inflatable annular member having a central opening and an organ contacting surface, a vacuum distribution element configured to create a diffused vacuum space in the central opening, and a positioning element having a lumen coupled to a vacuum source and to the inflatable annular member. The subject devices are suitable for use in a variety of surgical approaches and, as such, may be configured to be inserted into a patient's chest cavity through a sheath. Methods are also provided for using the subject devices, where the order of the methods may be altered. Also provided are systems and kits for manipulating and positioning an organ.

39 Claims, 5 Drawing Sheets

U.S. PATENT DOCUMENTS

| | | |
|---|---|---|
| 3,807,406 A | 4/1974 | Rafferty et al. |
| 3,858,926 A | 1/1975 | Ottenhues |
| 3,882,855 A | 5/1975 | Shulte et al. |
| 3,912,317 A | 10/1975 | Ohnaka et al. |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Priest et al. |
| 4,052,980 A | 10/1977 | Grams et al. |
| 4,094,484 A | 6/1978 | Galione et al. |
| 4,096,853 A | 6/1978 | Weigand |
| 4,096,864 A | 6/1978 | Kletschka et al. |
| 4,217,890 A | 8/1980 | Owens |
| 4,226,228 A | 10/1980 | Shin et al. |
| 4,230,119 A | 10/1980 | Blum |
| 4,300,564 A | 11/1981 | Furihata |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,904,012 A | 2/1990 | Nishiguchi et al. |
| 4,925,443 A | 5/1990 | Heilman et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,192,070 A | 3/1993 | Nagai et al. |
| 5,196,003 A | 3/1993 | Bilweis |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,290,082 A | 3/1994 | Palmer et al. |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cochen |
| 5,337,754 A * | 8/1994 | Heaven et al. ............... 600/562 |
| 5,348,259 A | 9/1994 | Blanco et al. |
| 5,363,882 A | 11/1994 | Chikama |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,453,078 A | 9/1995 | Valentine et al. |
| 5,456,714 A | 10/1995 | Owen |
| 5,467,763 A | 11/1995 | McMahon et al. |
| 5,480,425 A | 1/1996 | Ogilive |
| 5,484,391 A | 1/1996 | Buckman, Jr. et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,632,746 A | 5/1997 | Middleman et al. |
| 5,651,378 A | 7/1997 | Matheny et al. |
| 5,662,300 A | 9/1997 | Michelson |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,795,291 A | 8/1998 | Koros et al. |

| | | |
|---|---|---|
| 5,797,960 A | 8/1998 | Stevens et al. |
| 5,799,661 A | 9/1998 | Boyd et al. |
| 5,807,243 A | 9/1998 | Vierra et al. |
| 5,813,410 A | 9/1998 | Levin |
| 5,818,231 A | 10/1998 | Smith |
| 5,836,311 A | 11/1998 | Borst et al. |
| 5,864,275 A | 1/1999 | Ohashi et al. |
| 5,865,730 A | 2/1999 | Fox et al. |
| 5,868,763 A | 2/1999 | Spence et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A | 5/1999 | Corey, Jr. et al. |
| 5,906,607 A | 5/1999 | Taylor et al. |
| 5,908,378 A | 6/1999 | Kovacs et al. |
| 5,921,979 A | 7/1999 | Kovacs et al. |
| 5,927,284 A | 7/1999 | Borst et al. |
| 5,947,896 A | 9/1999 | Sherts et al. |
| 5,957,835 A | 9/1999 | Anderson et al. |
| 5,967,973 A | 10/1999 | Sherts et al. |
| 5,976,069 A | 11/1999 | Navia et al. |
| 5,976,080 A | 11/1999 | Farascioni et al. |
| 5,984,864 A | 11/1999 | Fox et al. |
| 6,007,486 A | 12/1999 | Hunt et al. |
| 6,010,531 A | 1/2000 | Donlon et al. |
| 6,013,027 A | 1/2000 | Khan et al. |
| 6,015,378 A | 1/2000 | Borst et al. |
| 6,015,427 A | 1/2000 | Mueller et al. |
| 6,019,722 A | 2/2000 | Spence et al. |
| 6,027,476 A | 2/2000 | Sterman et al. |
| 6,029,671 A | 2/2000 | Stevens et al. |
| 6,030,392 A | 2/2000 | Dakov |
| 6,032,672 A | 3/2000 | Taylor |
| 6,033,362 A | 3/2000 | Cohn |
| 6,036,641 A | 3/2000 | Taylor et al. |
| 6,036,703 A | 3/2000 | Evans et al. |
| 6,042,539 A | 3/2000 | Harper et al. |
| 6,043,273 A * | 3/2000 | Duhaylongsod ............ 514/478 |
| 6,050,266 A | 4/2000 | Benetti et al. |
| 6,110,187 A | 8/2000 | Donlon |
| 6,120,436 A | 9/2000 | Anderson et al. |
| 6,139,492 A | 10/2000 | Vierra et al. |
| 6,149,583 A | 11/2000 | Vierra et al. |
| 6,159,201 A | 12/2000 | Hamilton et al. |
| 6,183,486 B1 | 2/2001 | Snow et al. |
| 6,193,652 B1 | 2/2001 | Berky et al. |
| 6,210,323 B1 | 4/2001 | Gilhuly et al. |
| 6,213,940 B1 | 4/2001 | Sherts et al. |
| 6,213,941 B1 | 4/2001 | Beneti et al. |
| 6,231,585 B1 | 5/2001 | Takahashi et al. |
| 6,251,065 B1 | 6/2001 | Kochamba |
| 6,264,605 B1 | 7/2001 | Scirica et al. |
| 6,315,717 B1 * | 11/2001 | Benetti et al. ............. 600/210 |
| 6,328,688 B1 | 12/2001 | Borst et al. |
| 6,334,843 B1 | 1/2002 | Borst et al. |
| 6,336,898 B1 | 1/2002 | Borst et al. |
| 6,338,712 B2 | 1/2002 | Spence et al. |
| 6,346,077 B1 | 2/2002 | Taylor et al. |
| 6,348,036 B1 | 2/2002 | Looney et al. |
| 6,350,229 B1 | 2/2002 | Borst et al. |
| 6,361,493 B1 | 3/2002 | Spence et al. |
| 6,364,826 B1 | 4/2002 | Borst et al. |
| 6,371,906 B1 | 4/2002 | Borst et al. |
| 6,371,910 B1 | 4/2002 | Zwart et al. |
| 6,375,611 B1 | 4/2002 | Voss et al. |
| 6,390,976 B1 | 5/2002 | Borst et al. |
| 6,394,948 B1 | 5/2002 | Borst et al. |
| 6,394,951 B1 * | 5/2002 | Taylor et al. ............. 600/210 |
| 6,398,726 B1 | 6/2002 | Ramans et al. |
| 6,406,424 B1 | 6/2002 | Williamson et al. |
| 6,447,443 B1 | 9/2002 | Keogh et al. |
| 6,458,079 B1 | 10/2002 | Cohn et al. |
| 6,464,629 B1 | 10/2002 | Boone et al. |
| 6,464,630 B1 | 10/2002 | Borst et al. |
| 6,468,265 B1 | 10/2002 | Evans et al. |
| 6,475,142 B1 | 11/2002 | Parsons et al. |
| 6,478,029 B1 | 11/2002 | Boyd et al. |
| 6,478,729 B1 | 11/2002 | Rogers et al. |
| 6,482,151 B1 | 11/2002 | Vierra et al. |
| 6,494,211 B1 | 12/2002 | Boyd et al. |
| 6,503,245 B2 | 1/2003 | Palmer et al. |
| 6,506,149 B2 | 1/2003 | Peng et al. |
| 6,537,212 B2 | 3/2003 | Sherts et al. |
| 6,565,508 B2 | 5/2003 | Scirica et al. |
| 6,589,166 B2 | 7/2003 | Knight et al. |
| 6,592,573 B2 | 7/2003 | Castaneda et al. |
| 6,607,479 B1 | 8/2003 | Kochamba et al. |
| 6,610,008 B1 | 8/2003 | Spence et al. |
| 6,610,009 B2 | 8/2003 | Person et al. |
| 6,641,575 B1 * | 11/2003 | Lonky ..................... 604/540 |
| 6,701,930 B2 | 3/2004 | Benetti et al. |
| 2002/0040182 A1 * | 4/2002 | Benetti et al. ............. 600/210 |
| 2002/0111537 A1 * | 8/2002 | Taylor et al. ............. 600/210 |
| 2002/0161285 A1 | 10/2002 | Spence et al. |

FOREIGN PATENT DOCUMENTS

| | | |
|---|---|---|
| DE | 9004513 | 6/1990 |
| DE | 4139695 A1 | 6/1993 |
| EP | 0 293 760 A2 | 12/1988 |
| EP | 0 293 760 A3 | 12/1988 |
| EP | 0 293 760 B1 | 12/1988 |
| EP | 0 630 629 A1 | 5/1994 |
| EP | 668 058 A1 | 2/1995 |
| EP | 0 791 330 A2 | 2/1997 |
| EP | 0 791 329 A1 | 8/1997 |
| EP | 0 808 606 A1 | 11/1997 |
| EP | WO 97/40738 | 11/1997 |
| EP | 0 820 721 A1 | 1/1998 |
| EP | 0 919 193 A1 | 2/1999 |
| GB | 168216 | 9/1921 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 96/40354 | 12/1996 |
| WO | WO 97/26828 A | 7/1997 |
| WO | WO 97/40752 | 11/1997 |
| WO | WO 98/37814 | 9/1998 |
| WO | WO 98/49944 | 11/1998 |
| WO | WO 99/60929 | 12/1999 |
| WO | WO 99/60930 | 12/1999 |
| WO | WO 00/10466 | 3/2000 |
| WO | WO 01/17437 | 3/2001 |
| WO | WO 01/58362 A1 | 8/2001 |

OTHER PUBLICATIONS

Ancalmo, N. and J. L. Ochsner: "A Modified Sternal Retractor," Ann. Thorac, Surg. 21 (1976) 174.

Angelini, G.D., M.D. et al., "A Fiber-Optic Retractor for Harvesting the Internal Mammary Artery," Ann. Thorac. Surg. (1990; 50:314-5).

Angelini, G.D., M.D., "A Simple, Inexpensive Method of Heart Retraction During Coronary Artery Bypass Surgery," Ann. Thora. Surg 46:46-247, Aug. 1988.

Anstadt, M.P. MD et al., "Direct Mechanical Ventricular Actuation for Cardiac Arrest in Humans," Chest, vol. 100, No. 1, Jul. 1991, pp. 86-92.

Antinori, C. et al., "A Method of Retraction During Reoperative Coronary Operations Using the Favaloro Retractor," The Society of Thoracic Surgeons: 1989.

Archer, R. Do et al., "Coronary Artery Revascularization Without Cardiopulmonary Bypass," Texas Heart Institute Journal, vol. 11, No. 1, Mar. 1984, pp. 52-57.

Ballantyne, C.M. et al. "Delayed Recovery of Severely 'Stunned' Myocardium With the Support of a Left Ventricular Assist Device after Coronary Artery Bypass Graft Surgery," Journal of the American College of Cardiology, vol. 10, No. 3, Sep. 1987, pp. 710-712.

Bedellino, M.M., et al., "The Cardiac Rag—Simple Exposure of the Heart," Texas Heart Institute Journal, vol. 15, No. 2, 1988, 134-35.

Beg, R.A. et al., "Internal Mammary Retractor," Ann Thorac, Surg., vol. 39, No. 1, Jan. 1985, pp. 286-287.

Benetti, F. J. et al., "Direct Coronary Surgery with Saphenous Vein Bypass Without Either Cardiopulmonary Bypass Graft or Cardiac Arrest," The Journal of Cardiovascular Surgery, vol. 26, No. 3, May-Jun. 1985, pp. 217-222.

Benetti, F. J. et al., "Direct Myocardial Revascularization Without Extracorporeal Circulation," Chest, vol. 100, No. 2, Aug. 1991, pp. 312-316.

Benetti, F. J., "Coronary Revascularization with Arterial Conduits via a Small Thoracotomy and Assisted by Thoracoscopy, Although Without Cardiopulmonary Bypass," Cor Europaeum 4 (1) 22-24 (1995).

Borst et al., "Coronary Artery Bypass Grafting Without Cardiopulmonary Bypass and Without Interruption of Native Coronary Flow Using a Novel Anastomosis Site Restraining Device ('Octopus')", JAAC vol. 27, No. 6, May 1996:1356-64.

C. Borst et al., entitled "Regional Cardiac Wall Immunobilization for Open Chest and Closed Chest Coronary Artery Bypass Grafting on the Beating Heart: The 'Octopus' Method," Circulation, (Oct. 15, 1995) vol. 92, No. 8 supplemental I,I-177.

Bugge, M., "A New Internal Mammary Artery Retractor," Thorac. Cardiovasc Surgeon 38, pp. 316-317 (1990).

Buffolo, E., et al., "Direct Myocardial Revascularization Without Cardiopulmonary Bypass," Thorac. Cardiovasc. Surgeon, 33 (1985) pp. 26-29.

Calafiore, A. M., et al:, "Minimally Invasive Coronary Artery Bypass Grafting," The Annals of Thoracic Surgery, 62:1545-8, 1996.

Calvin, I. F. & Newman, D.C., "Circumflex Exposure Using a Cardiac Sling," Ann Thorac Surg 1990:49:833-4.

Campalani, G., M.D., et al., "A New Self-Retaining Internal Mammary Artery Retractor," J. Cardiovas. Surg. 28, 1987, pp. 347-348.

Chaux, A. and Blanche, C., "A New Concept in Sternal Retraction: Applications for Internal Mammary Artery Dissection and Valve Replacement Surgery," Ann. Thorac. Surg. 42, Oct. 1986, pp. 473-474.

Cohen, A.S., et al., "Mini-Sternotomy for Coronary Artery Bypass Grafting," The Annals of Thoracic Surgery 1996; 62:1884-85.

Cutler, B.S. and Cantelmo, N.L., "New Use for an Old Clamp," Archives of Surgery—vol. 115, 1136-37, Sep. 1980.

Delacroix-Chevalier Surgical Instruments, IMA Saving Packages Brochure.

DelRossi, A J and Lemole, GM, "A New Retractor to Aid in Coronary Artery Surgery," The Annals of Thoracic Surgery, vol. 36, No. 1, 101-102, Jul. 1983.

Donald, I., "Snake Flexible Arm" British Medical Journal, Oct. 19, 1968, p. 170.

English abstract for Russian Patent No. SU 938967.

Fanning, W. J. et al., "Reoperative Coronary Artery Bypass Grafting Without Cardiopulmonary Bypass," The Annals of Thoracic Surgery, vol. 55, No. 2, Feb. 1993, pp. 486-489.

Favaloro, R. G., et al. "Direct Myocardial Revascularization by Saphenous Vein Graft," The Annals of Thoracic Surgery, vol. 10, No. 2, Aug. 1970, pp. 97-111.

Fonger, J. D., et al., "Enhanced Preservation of Acutely Ischmenic Myocardium with Transeptal Left Ventricular Assist," The Annals of Thoracic Surgery, vol. 57, No. 3, Mar. 1994, pp. 570-575.

Gacioch, G. M., MD, et al., "Cardiogenic Shock Complicating Acute Myocardial Infarction: The Use of Coronary Angioplasty and the Integration of the New Support Device into Patient Management," Journal of the American College of Cardiology, vol. 19, No. 3, Mar. 1, 1992.

Green, GE., "Technique of Internal Mammary-Coronary Artery Anastomosis," The Journal of Cardiovascular Surgery, 78:455-79, 1979.

Grundeman et al., "Vertical Displacement of the Beating Heart by the Octopus Tissue Stabilizer: Influence on Coronary Flow", Ann Thorac Surg 1998; 63: 138-152.

Grundeman et al., "Hemodynamic Changes During Displacement of the Beating Heart by the Utrecht Octopus Method", Ann Thorac Surg 1997; 66:576-579.

Guzman, F. M.D., "Transient Radial Nerve Injury Related to the Use of A Self Retraining Retractor for Internal Mammary Artery Dissection," J. Cardiovasc. Surg. 30, 1989, pp. 1015-1016.

Hasan, R. I., et al., "Technique of Dissecting the Internal Mammary After Using The Moussalli Bar," European Journal of Cardio Thoracic Surgery, 4:571-572, 1990.

Itoh, Toshiaki, M.D., et al.,"New Modification of a Mammary Artery Retractor," Ann. Thorac. Surg. 9, 1994; 57:1670-1.

Jansen et al., "Experimental Off-Pump Grafting of a Circumflex Brach via Sternotomy Using a Suction Device", Ann Thorac Surg 1997; 63:S93-6.

Jansen et al., "Off-Pump Coronary Bypass Grafting: How to Use the Octopus Tissue Stabilizer," Ann Thorac Surg 1998; 66:576-9.

Japanese Journal of Thoracic Surgery, vol. 42, No. 2, 1989.

Japanese Article "Heart Retractor".

Janke, W. H., "Heart Support for Coronary Bypass Surgery Involving the Circumflex Artery System," The Journal of Thoracic and Cardiovascular Surgery, pp. 883-884.

Kolessov, V.I., M.D., "Mammary Artery-Coronary Artery Anastomosis as Method of Treatment for Angina Pectoris," Thoracic and Cardiovascular Surgery, vol. 54, No. 4, Oct. 1967, pp. 535-544.

Kazama, S. et al., "Fabric Heart Retractor for Coronary Artery Bypass Operations," The Annals of Thoracic Surgery, 55:1582-3, 1993.

Kresh, J. Y., et al., "Heart-Mechanical Assist Device Interaction," Trans. Am. Soc. Artif. Intern. Organs, vol. XXXII, 1986, pp. 437-443.

Lavergne, et al., "Transcatheter Radiofrequency Ablation of Atrial Tissue Using a Suction Catheter," PACE, vol. 12, Jan. 1989, Part II, pp. 177-186.

Lonn, U., M.D., et al., "Coronary Artery Operation Supported by the Hemopump: An Experimental Study on Pigs," The Annals of Thoracic Surgery, vol. 58, No. 1, Jul. 1994, pp. 516-523.

Matsuura, A., et al., "A New Device for Exposing the Circumflex Coronary Artery," The Annals of Thoracic Surgery, 59:1249-50, 1995, pp. 1249-1250.

McGee, M. G.,et al., "Extended Clinical Support with an Implantable Left Ventricular Assist Device," Trans. Am. Soc. Artif. Intern. Organs, vol. XXXV, 1989, pp. 614-616.

McKeown, P.P. et al., "A Modified Sternal Retractor for Exposure of the Internal Mammary Artery," Ann. Thorac. Surg. 32 (1981) 619.

Ochsner, J. L., et al., "Surgical Management of Diseased Intracavitary Coronary Arteries," The Annals of Thoracic Surgery, vol. 38, No. 4, Jul. pp. 356-362, Oct. 1984.

Parsonnet, V. MD, et al., "Graduated probes for Coronary Bypass Surgery," The Journal of Thoracic and Cardiovascular Surgery, vol. 68, No. 3, 424-26 (Sep. 1974).

Parsonnet, V. MD, et al., "Self—Retaining Epicardial Retractor for Aortocoronary Bypass Surgery," The Journal of Thoracic and Cardiovascular Surgery, 629-30 1979.

Pfister, A. J. M.D., et al., "Coronary Artery Bypass Without Cardiopulmonary Bypass," The Annals of Thoracic Surgery, vol. 54, No. 6, Dec. 1992, pp. 1085-1092.

Phillips, Steven J., M.D. et al., "A Versatile Retractor for Use in Harvesting the Internal Mammary Artery and Performing Standard Cardiac Operations," J. Thorac. Cardiovasc. Surg. (1989;97:633-5).

Pilling Surgical Instruments, A Rusch International Company Brochure.

Pittman, John, M.D., et al., "Improved Visualization of the Internal Mammary Artery with a New Retractor System," Ann. Thorac. Surg., 1989; 48:869-70.

Riahi, M.,et al., "A Simple Technique and Device to Provide a Bloodless Operative Field in Coronary Artery Surgery Without Cross-Clamping the Aorta," The Journal of Thoracic and Cardiovascular Surgery, vol. 66, No. 6, Dec. 1973, pp. 974-978.

Richenbacher, W. E., MD, et al., "Current Status of Cardiac Surgery: A 40-Year Review," Journal of American College of Cardiology, vol. 14, No. 3, pp. 535-544.

Robicsek, F., "Aortic Spoon-Jaw Clamp for Aorto-Saphenous Vein Anastomosis," J. Card. Surg., 1995; 10:583-585.

Robinson, M. C., et al., "A Minimally Invasive Surgical Method for Coronary Revascularization—Preliminary Experience in Five Patients," Circulation, Oct. 15, 1995, vol. 92, No. 8, 1-176.

Rousou, J. et al., "Cardiac Retractor for Coronary Bypass Operations," Ann Thorac. Surg, 1991; 52:877-8.

Roux, D., M.D. et al., "Internal Mammary Artery Dissection: A Three Dimensional Sternal Retractor," J. Cardiovasc. Surg., 1989; 30:996-7.

Roux, D., M.D. et al., "New Helper Instrument in Cardiac Surgery," Ann. Thorac. Surg., 1989, 48:595-596.

Ruzevich, S. A., et al., "Long-Term Follow-Up of Survivors of Postcardiotomy Circulatory Support," Trans. Am. Soc. Artif. Intern. Organs, vol. XXXIV, 1988, pp. 116-124.

Scholz, K. H., et al., "Transfemoral Placement of the Left Ventricular Assist Device 'Hemopump' During Mechanical Resuscitation," Thoracic and Cardiovascular Surgeon, vol. 38 (1990) pp. 69-72.

Splittgerber et al., "Exposing the Circumflex Coronary Artery: The Heartflip Technique," Ann Thorac Surg. 1996;61:1019-20.

Stevens, et al., "Closed Chest Coronary Artery Bypass With Cardioplegic Arrest in the Dog," 67th Scientific Session, 238, I-251.

Takahashi et al., "A New Instrument for Immobilization and Hemostasis During Minimally Invasive Direct Coronary Artery Bypass ('MIDCAB doughnut'): Experimental Study", J Card Surg 1997; 12:185-189.

Trapp, et al., "Placement of Coronary Artery Bypass Graft without Pump Oxygenator," Journal of the Society of Thoracic Surgeons and The Southern Thoracic Surgeons Assn. vol. 19, No. 1, Jan. 1975.

Trapp W.G., "To Use or Not To Use the Pump Oxygenator in Coronary Bypass Operations," The Annals of Thoracic Surgery, vol. 19, No. 1, Jan. 1975, pp. 108-109.

USSC Cardiovascular Thora-Lift™, United States Surgical Corporation, Norwalk, Connecticut, Product Brochure.

Vincent, J.G., "A Compact Single Post Internal Mammary Artery Dissection Retractor," Eur. J. Cardio-Thor. Surg. 3 (1989) 276-277.

Westaby, S., "Coronary Surgery Without Cardiopulmonary Bypass," British Heart Journal vol. 73 pp. 203-205, 1995.

Westaby, S. et al., "Less Invasive Coronary Surgery: Consensus From the Oxford Meeting," The Annals of Thoracic Surgery, 62:924-31, 1996.

Zumbro, G. L. et al., "A Prospective Evaluation of the Pulsatile Assist Device," The Annals of Thoracic Surgery, vol. 28, No. 2, Aug. 1979, pp. 269-273.

* cited by examiner

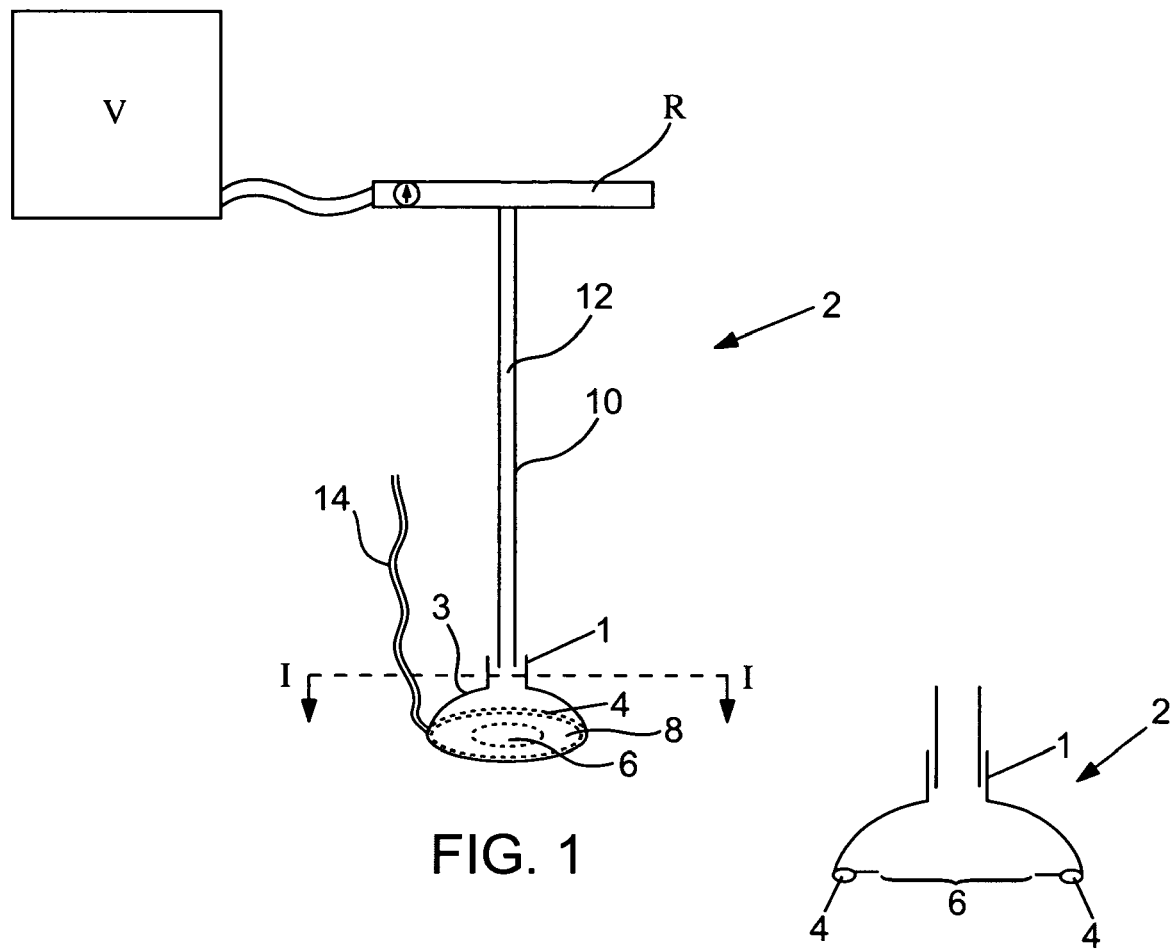
FIG. 1
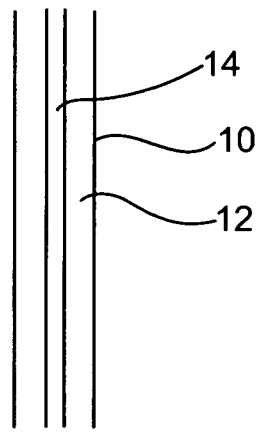
FIG. 1B
FIG. 1A

ORGAN MANIPULATOR AND POSITIONER AND METHODS OF USING THE SAME

FIELD OF THE INVENTION

The field of this invention is organ manipulation and support, specifically manipulation and support of a heart and more specifically a beating heart.

BACKGROUND OF THE INVENTION

Coronary artery bypass grafting (CABG) has traditionally been performed with the use of a cardiopulmonary bypass (CPB) machine to oxygenate and perfuse the body during surgery. Recently, techniques have been developed to allow for performing CABG without the use of CPB by stabilizing the epicardial surface of the beating heart at the coronary anastomosis site with a stabilizer of some sort to allow placement of sutures through the graft vessel and recipient coronary artery. This procedure may be performed through a sternotomy, mini-sternotomy, thoracotomy or mini-thoracotomy, or less invasively through a port provided within the chest cavity of the patient, e.g., between the ribs or in a subxyphoid area, with or without the visual assistance of a thoracoscope.

Oftentimes, one or more arteries of interest are located on the lateral or posterior aspects of the heart, making access to such arteries difficult, especially in a minimally invasive procedure such as port access and the like. For other arteries, access is typically not so problematic, for example if the left anterior descending (LAD) artery is the artery of interest, access is easily accomplished using either a sternotomy or a thoracotomy approach. However, oftentimes other arteries may be involved in the bypass procedure. For example, the patient may require bypass to multiple coronary arteries, including the circumflex artery (CxA) on the left lateral aspect of the heart, the right coronary artery (RCA) on the right lateral aspect of the heart, and the posterior descending artery (PDA) on the back side of the heart. It is very difficult to access the CxA, RCA, and PDA without a sternotomy, as the heart needs to be turned and/or tilted significantly to give a surgeon access to its side or back and, with an intact sternum, insufficient space exists for these maneuvers of the heart. When a sternotomy is performed, the apex of the heart is generally lifted out of the body through the sternotomy in order to reach the PDA. Contrarily, in minimally invasive procedures such as closed chest procedures and the like, arteries located on the lateral and/or posterior aspects of the heart are extremely difficult to access because the heart can not be so easily manipulated.

An additional challenge to heart manipulation during beating heart surgery is that some hearts do not hemodynamically tolerate manipulation well. Thus, even if the heart could be sufficiently manipulated to enable access to lateral and posterior arteries, it must be done with minimal or no adverse hemodynamic consequences. Conventional techniques and devices employed to manipulate the heart typically suffer from one or more disadvantages including cardiac contraction and expansion constraint, limited use, e.g., useful only for arrested hearts and limited range of motion.

For example, a common technique used with a sternotomy approach involves the use of pericardial sutures to retract the heart into the proper position for surgery. However, conventional use of pericardial sutures for retraction of a beating heart is inconvenient and potentially harmful to the patient. In such a procedure, the pericardium is incised and sutures are inserted along cut edges of the pericardium, and then tension is exerted on the sutures to move the heart together as a unit with the pericardium. When the sutures are pulled to lift the heart (with the pericardium), compressive force exerted by the pericardium on at least one side of the heart sometimes constrains cardiac contraction and expansion.

U.S. Pat. No. 5,799,661 to Boyd, et al., describes (with reference to FIGS. 33A–33C) a suction cup-shaped manipulator on a long shaft. The suction cup is to be attached to an arrested heart by suction, and the device is then used to move the heart within the chest cavity. A vacuum is applied to the cup to provide suction, and the vacuum is said preferably to have a value not less than −150 mmHg (to avoid tissue damage). The suction cup is made of a soft, flexible elastomeric material such as silicone rubber, has a diameter of approximately 12 mm to 50 mm, and has a textured, high friction distal surface (for gripping the heart). The high friction can be achieved by a pattern of bumps or an absorbent high friction material (such as non-woven polyester fabric).

The suction cup of U.S. Pat. No. 5,799,661 is apparently flexible relative to the distal end of a rigid shaft. However, U.S. Pat. No. 5,799,661 does not teach attaching the suction cup to the shaft by a joint or other mechanical element to provide limited freedom to translate along a first axis and/or freedom to rotate about the first axis. Without such provisions to allow a beating heart to translate and/or rotate in a manner which does not negatively effect hemodynamics, the suction cup apparatus described in U.S. Pat. No. 5,799,611 is useful only to retract an arrested heart.

Accordingly, there is continued interest in the development of new devices and methods for use for easily and effectively manipulating and supporting an organ such as a beating heart without compromising the hemodynamic stability thereof. In other words, there is a need for organ manipulation and support devices and methods of use capable of physically translating a beating heart from its natural resting place to a location better suited to surgical access, and then holding the beating heart in the latter location during surgery without compressing (or otherwise deforming) the heart or great vessels in such a way that hemodynamic function is compromised. Of particular interest would be the development of such devices and methods of use which may be used in a variety of surgical approaches, including a full and partial sternotomy, a full and partial thoracotomy and port access or endoscopic or thoracoscopic procedures and used with a variety of organs.

SUMMARY OF THE INVENTION

Devices and methods are provided for manipulating and supporting an organ, e.g., a beating heart. The subject devices are characterized by having an inflatable annular member having a central opening and an organ contacting surface, a vacuum distribution element configured to create a diffused vacuum space in the central opening, and a positioning element having a lumen coupled to a vacuum source and to the inflatable annular member, wherein the positioning element is configured to position the inflatable annular member and provide a vacuum source thereto. The subject devices are suitable for use in a variety of surgical approaches including sternotomies, mini-sternotomies, thoracotomies or mini-thoracotomies, or through a port provided within the chest cavity of the patient, e.g., between the ribs or in a subxyphoid area, with or without the visual assistance of a thoracoscope and, as such, may be configured to be inserted into a patient's chest cavity through a sheath. Methods are also provided for using the subject devices, where the order of the steps of the subject methods may be altered. Also provided are systems and kits for manipulating and positioning an organ.

It is an aspect of the invention to provide an organ manipulating and positioning device and methods of use that can be introduced into a body cavity through a wide variety of access means including a sternotomy, mini-sternotomy, thoracotomy or mini-thoracotomy, or less invasively through a port provided within the chest cavity of the patient, e.g., between the ribs or in a subxyphoid area, with or without the visual assistance of an thoracoscope.

It is yet another aspect of the invention to provide an organ manipulating and positioning device and methods of use that can be introduced into a body cavity through a sheath.

It is yet another aspect of the invention to provide an organ manipulating and positioning device and methods of use that can be used with a wide variety of organs, including a heart and more specifically a beating heart.

It is yet another aspect of the invention to provide an organ manipulating and positioning device and methods of use that do not produce clinically significant hemodynamic instability.

It is an advantage that the subject invention can be resiliently deformed in a deflated state for retention inside a sheath.

It is yet another advantage that the subject invention can conform to a surface of an organ.

It is yet another advantage that the subject invention is capable of sufficiently moving both axially or vertically and laterally to correspond to organ movement.

It is yet another advantage that the subject invention is atraumatic.

It is yet another advantage that the subject invention is capable of manipulating and positioning an organ without any clinically significant hemodynamic instability.

These and other aspects, advantages and features of the present invention will become apparent to those persons skilled in the art upon reading the details of the presently described invention.

BRIEF DESCRIPTION OF THE DRAWINGS

FIG. 1 shows an exemplary embodiment of an organ manipulator and positioner according to the present invention. FIG. 1A shows the positioning element of the device of FIG. 1 having an inflatable annular member inflation line disposed within the lumen of the positioning element. FIG. 1B shows a cross-sectional view of the subject device of FIG. 1, taken along section line I—I in FIG. 1.

DETAILED DESCRIPTION OF THE INVENTION

Figure 2:
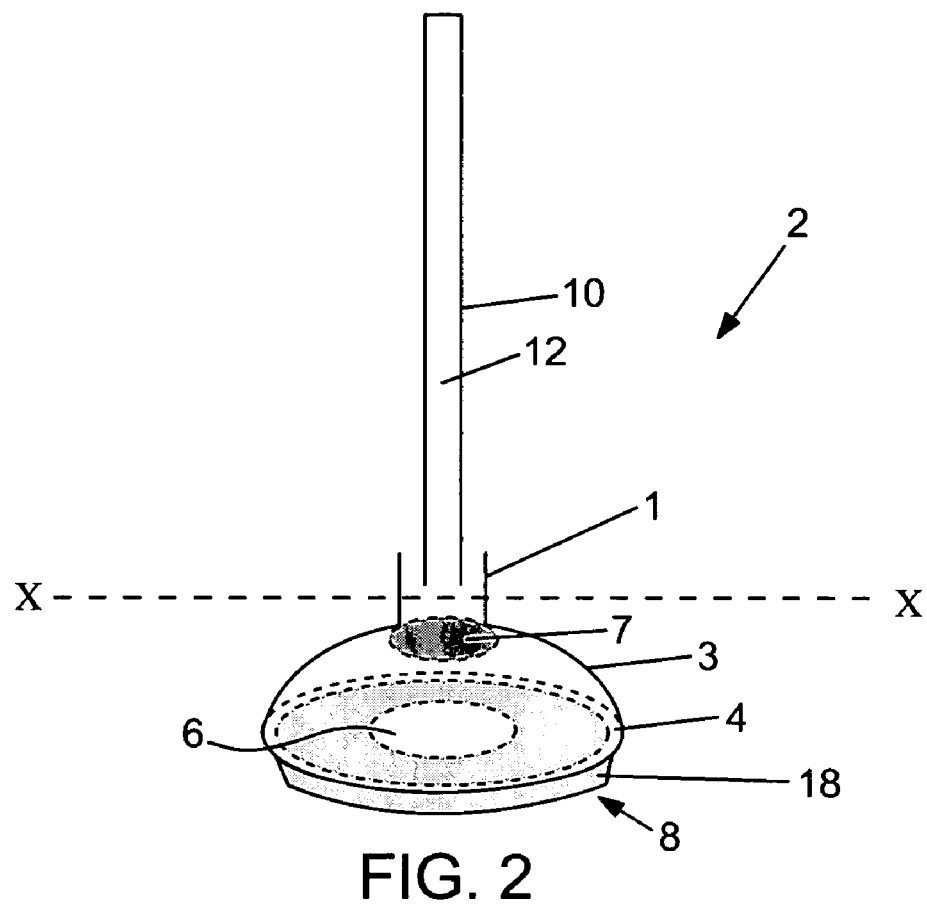
FIG. 2 shows an enlarged view of an exemplary embodiment of an inflatable annular member of the present invention.

Devices and methods are provided for manipulating and supporting an organ, e.g., a beating heart. Among the numerous beneficial features of the inventions described herein, the subject devices may be characterized by having an inflatable member having a central opening and an organ contacting surface, a vacuum distribution element configured to create a diffused vacuum space in the central opening, and a positioning element having a lumen coupled to a vacuum source and to the inflatable annular member, wherein the positioning element is configured to position the inflatable annular member and provide a vacuum source thereto. The subject devices are suitable for use in a variety of surgical approaches including sternotomies, mini-sternotomies, thoracotomies or mini-thoracotomies, or through a port provided within the chest cavity of the patient, e.g., between the ribs or in a subxyphoid area, with or without the visual assistance of a thoracoscope and, as such, may be configured to be inserted into a patient's chest cavity through a sheath. Methods are also provided for using the subject devices, where the order of the methods may be altered. Also provided are systems and kits for manipulating and positioning an organ.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a reagent" includes a plurality of such reagents and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Devices

As summarized above, devices are provided for manipulating and supporting an organ, such as a beating heart. Generally, the devices include an inflatable member which is configured to have a central opening defining a vacuum space and an organ contacting surface, where in many embodiments the organ contacting surface includes an atraumatic, compliant material. The central opening of the inflatable member includes a vacuum distribution element configured to create a distributed or diffused vacuum space in the central opening, in other words it provides a means to diffuse the suction exerted on the organ. The inflatable member is coupled to a positioning element having a lumen therethrough, where such a lumen is also coupled to a vacuum source. Thus, the positioning element is configured to position the inflatable member at a target site and provide a vacuum source thereto to engage the device with the organ of interest. Although a variety of shapes and configurations are possible, the inflatable member is preferably annular.

The subject devices are suitable for use with a variety of surgical approaches, including both open and closed chest procedures. In other words, the devices are suitable for use with both open or closed chest procedures, such as sternotomies, mini-sternotomies, thoracotomies or mini-thoracotomies, or through a port provided within the chest cavity of the patient, e.g., between the ribs or in a subxyphoid area, with or without the visual assistance of a thoracoscope. As such, the compliant nature of the subject devices, i.e., the ability of the devices to be resiliently deformed into a deflated state, enables them to be delivered to the surgical site through a circumferentially restraining or enclosing member, such as a sheath or cannula or the like, for example during such minimally invasive or closed-chest procedures.

Similarly, the subject devices are suitable for manipulating and supporting a variety of organs, where representative organs include, but are not limited to, hearts such as beating hearts, stomachs, gall bladders, livers, spleens, intestines, etc. In further describing the subject devices, reference to a beating heart will be used as an example, and not a limitation, of a suitable organ; however, the subject devices may be used with a variety of surgical procedures and organs, as described above, all of which are within the scope of the present invention. Furthermore, the subject devices may be single-use or re-useable devices, i.e., the devices may be adapted to be sterilized for multiple uses.

The subject devices will now be further described with respect to the figures, where like numerals represent like features or components. FIG. 1 shows an exemplary device according to the subject invention. Accordingly, the device 2 of FIG. 1 includes an inflatable annular member 4 having a central opening 6 covered on one side by a cover 3 and an organ contacting surface 8. The inflatable annular member 4, more specifically the cover 3 of the inflatable annular member 4, is coupled to a positioning element 10 having at least one lumen 12 therethrough by an attachment means 1. As such, the proximal end of the positioning element, more specifically the proximal end of the lumen 12 of the positioning element 10, is coupled to a flow regulator R and vacuum source V, while the distal end is coupled to the cover 3 associated with the inflatable annular member 4, where such a regulator R and vacuum source V provide regulated suction to an organ such that the pressure surrounding the central opening of the device is reduced by opening suction flow regulator R, thus enabling suction to be applied to the organ of interest in such a way that the organ can be moved by moving the device. In certain embodiments of the subject invention, the device may include a plurality of inflatable annular members. For example, a subject device may have from about one to ten inflatable annular members, usually from about one to six inflatable annular members, and more usually from about one to two inflatable annular members. However, depending on the particular application, a subject device may include a greater or fewer number of inflatable annular members. In those embodiments employing a plurality of inflatable annular members, the inflatable annular members may be positioned in any convenient manner. For example, the inflatable annular members may be positioned in a row, concentrically, stacked, etc., or any other suitable arrangement.

The device 2 may also include an inflatable annular member inflation line 14, for inflation of the annular member, typically in situ, where the inflatable annular member inflation line 14 may be positioned adjacent the positioning element 10, such that the inflatable annular member inflation line 14 and the positioning element are spaced apart, or the inflatable annular member inflation line 14 may be positioned within the positioning element 10, as shown in FIG. 1A. Accordingly, FIG. 1A shows a positioning element 10 of the subject invention having an inflation line 14 disposed therein. Oftentimes, the inflation line 14 is a flexible line. In those embodiments including a plurality of inflatable annular members, any convenient means for inflating each annular element may be employed. For example, a single inflation line may be used to inflate all the annular members or each annular member may be inflated with a respective inflation line, or two or more chambers/members may have a vent hole fluidly interconnecting them. The plurality of inflatable annular members may be inflated at the same time or at different times.

FIG. 1B shows a cross-sectional view of the inflatable annular member 4 and cover 3 of FIG. 1, taken along section line I—I in FIG. 1.

FIG. 2 shows a perspective, enlarged view of the inflatable annular member 4 of FIG. 2. The inflatable annular member 4 of the subject invention may take any of a variety of shapes ranging from simple to complex, where the particular shape of the annular member may depend on a variety of factors including, but not limited to, the surgical approach used, i.e., open or closed chest, the surgical procedure performed, e.g., beating heart CABG, and the like. For example, the shape of an inflatable annular member may be of a substantially rectangular, substantially square, substantially circular, substantially round, substantially oblong, substantially elliptical and substantially oval shape, etc. Alternatively, as mentioned, the shape may be more complex such as a substantially irregular shape, and the like.

Likewise, the cross sectional shape of the inflatable annular member may vary and include both simple and complex shapes. For example, the cross sectional shape of an inflatable annular member may be of a substantially rectangular, substantially square, substantially circular, substantially round, substantially oblong, substantially elliptical or substantially oval shape, etc. Alternatively, as mentioned, the cross sectional shape may be more complex such as a substantially irregular shape, and the like.

Similarly, the size of the subject annular member may vary depending on a variety of factors including, but not limited to, the surgical approach used, i.e., open or closed chest, the surgical procedure performed, e.g., beating heart CABG, and the like. For example, when use to engage an adult human heart, and more specifically the apex of an adult human heart, the diameter of the inflatable annular member, rather the diameter of the central opening of the inflatable annular member, may range from about 5 mm to about 50 mm.

The subject inflatable annular member 4 and associated cover 3 may be made from a variety of materials, typically polymers, where representative materials include, but are not limited to, elastomers, polyurethane, polyester, polyamide, polyimides, and the like, where the inflatable annular member 4 and cover 3 may be made from the same or different materials. For example, polyurethane having a material thickness of from about 0.001 inches to about 0.010 inches may be used. Two examples which were constructed used 0.002 inch thick polyurethane and 0.004 inch polyurethane, respectively. Whether or not the inflatable annular member and cover are made from the same material or different materials, the inflatable annular member and cover may be a unitary piece of construction or may be separate pieces or components operatively associated together to form a functional unit.

A feature of the subject inflatable annular member is that it is atraumatic, i.e., it does not adversely effect the organ of interest or any surrounding tissue, etc., that may also be contacted by the subject devices during the procedure. In other words, the inflatable annular member 4 does not significantly harm or damage the organ to which it is contacted or any surrounding organs and structures, i.e., the use of the device does not result in a clinically relevant adverse effect on the organ. As such, the inflatable annular member is typically manufactured such that all seams are on the interior of the inflatable annular member. More specifically, the inflatable annular member 4 is manufactured such that after the seams or interfaces of the inflatable annular member 4 are operatively associated together, e.g., by heat welds, radiofrequency (RF) energy welds, or the like, the inflatable annular member is everted to a working configuration so that all material interfaces or seams are positioned on the inside of the inflatable annular member 4 after such an eversion so that the outside surface of the inflatable annular member 4 is substantially smooth or free of such outwardly protruding seams, etc. As will be apparent to those of skill in the art, such a manufacturing technique and resultant device advantageously minimizes the likelihood that the device will damage the target organ or surrounding tissue or structures.

To inflate the annular member 4 of the subject device, a variety of substances can be used. In many embodiments of the subject device, the inflatable annular member 4 is inflated with a gas such as oxygen, nitrogen, carbon dioxide and inert gases such as helium, neon, argon, air and the like. However, the inflatable annular member may also be inflated with substances or agents other than gas, for example a fluidic substance such as saline, water, contrast solution, etc., or any combination thereof, may be employed to inflate the annular member 4.

A feature of the inflatable annular member 4 of the subject device is that it is resiliently deformed into a deflated state, where such a feature facilitates advancement of the inflatable annular member 4 to a target site. Accordingly, the subject inflatable annular member 4 is configured to be inflated to assume an inflated, organ contacting or working configuration as shown in FIGS. 1, 1B, 2, 2A, 3, 4, 5 and 8. In other words, when deflated, the subject annular member 4 assumes a lower profile or compacted configuration, which enables it to be easily navigated to a target site, such as a site of a heart, and then inflated via the inflation line. In many embodiments of the subject device, the inflatable annular member 4 is deflated in such a manner to enable it to be positioned and retained within a sheath such as a cannula for insertion into the body, e.g., for insertion through a port positioned in a chest wall during closed chest procedures such as closed chest CABG procedures, ablation for arrhythmias or cellular cardiomyoplasty, for example. However, even if used with open chest procedures, the device may still be introduced to the target site in a deflated state.

As mentioned above, the inflatable annular member 4 may include an atraumatic, compliant material positioned on the organ contacting side of the annular member, i.e., positioned such that it contacts the organ of interest to conform to and create a seal therewith, so that the device 2 can lift the organ by exerting suction thereon without causing therapeutically or clinically significant adverse effects. FIG. 2 shows an exemplary embodiment of the subject device 2 having an atraumatic, compliant material 18 operatively positioned thereon, shown herein as positioned on device 2 of FIG. 1. Accordingly, as shown in FIG. 2, device 2 includes a soft, compliant material 18 associated with the organ contacting side 8 of the inflatable annular member 4, where such a soft, compliant material 18 positioned on the organ contacting side 8 of a subject device serves to enhance the seal formed with the organ with which it contacts. Compliant material 18 may also facilitate distribution of vacuum over a greater area, such as by diffusing the suction exerted on the organ, and may deter or substantially minimize the likelihood that organ tissue will be sucked into the central opening of the device. For example, the atraumatic, compliant material 18 may be configured to conform to the apex of a heart and, when contacted with the heart under vacuum, distribute the vacuum over the area of the soft, compliant material 18 and create an intimate seal with the apex of the heart. Because the soft, compliant material 18 contacts the organ, it is usually made from a biocompatible material such as biocompatible foam, e.g., biocompatible polyurethane foam, gel, fabric, e.g., non woven rayon/viscose fabric, gauze, material of the type conventionally used in neuro sponges, or other foam which is biocompatible and suitable for this purpose, and the like, where biocompatible foam having closed cells is of particular interest. The atraumatic, compliant material 18 may be associated with the inflatable annular member 4 by any convenient means, e.g., a biocompatible adhesive may be employed, where representative adhesives include, but are not limited to, Silastic medical adhesive available from Dow Corning of Midland, Mich. and Loctite 4541 or Loctite 4011 available from Henkel Technologies of Dusseldorf, Germany, ultraviolet cured adhesives (e.g., Dymax 190M or Dymax 1-20270 (Dymax Corporation, Torrington, Conn.) or elastomer-toughened cyanoacrylates. The atraumatic, compliant material 18 may be associated with the entire organ contacting area 8 of the inflatable annular member 4 or may be associated with only a portion of the organ contacting area 8 of the inflatable annular member 4.

The subject inflatable annular member may also include a vacuum distribution element, such as open-cell (reticulated) foam, or other structure able to pass air therethrough, operatively associated with the central opening 6 of the inflatable annular member 4 and configured to distribute the vacuum or suction over a larger area than would be distributed otherwise (in other words than would be distributed without an element for distributing the vacuum), i.e., configured to diffuse the vacuum or suction exerted on the organ. As will be apparent to one of skill in the art, such vacuum distribution advantageously minimizes the likelihood that an organ's tissue will be suctioned into the lumen providing the vacuum source.

Figure 2A:
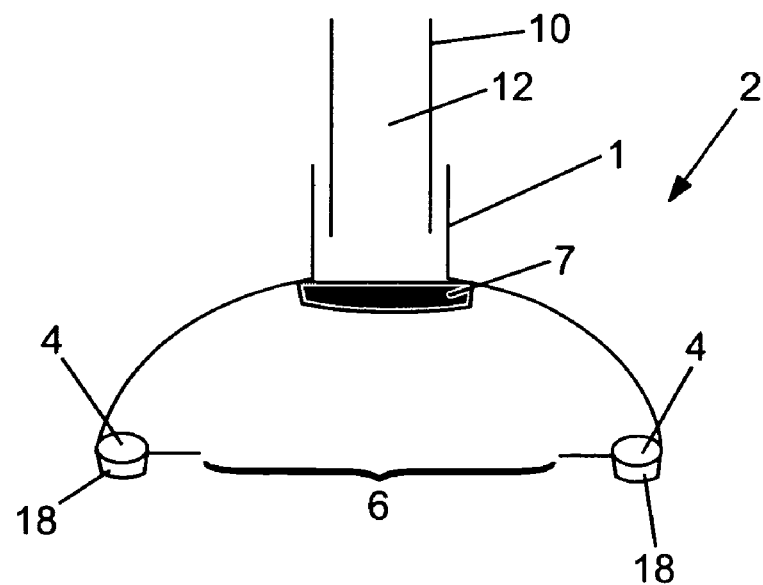
FIG. 2A shows a cross-sectional view of the subject device of FIG. 2, taken along section line X—X in FIG. 2.

FIG. 2 shows an exemplary embodiment of a subject device 2 having a vacuum distribution element 7 for distributing vacuum. As such, the vacuum distribution element 7 is positioned adjacent the lumen 12 of the positioning element 10, through which vacuum is supplied to the organ of interest. A vacuum distribution element 7 may be made of a variety of materials, provided that the material employed enables the vacuum to be diffused or spread over its surface. Representative materials include, but are not limited to, foam such as open cell foam, e.g., biocompatible polyurethane foam, fabric, e.g., non woven rayon/viscose fabric, gauze, material of the type conventionally used in neuro sponges, and the like. Similarly, the material may be associated or attached to the inflatable annular member 4, or rather the cover 3 of the inflatable annular member 4, using any convenient means, where examples of suitable attachment means include, but are not limited to, adhesives, elastic cinches, heat welding, RF welding, ultrasonic welding, and the like. FIG. 2A shows a cross-sectional view of the device 2 of FIG. 2, taken along section line X—X in FIG. 2. The subject device 2 in FIG. 2 thus includes a positioning element 10, an attachment means 1, a vacuum distribution element 7 and an inflatable annular member 4.

As mentioned above, the inflatable annular member 4 is coupled to a positioning element 10 having at least one lumen 12 therethrough, through which vacuum is applied to the target organ. That is, the positioning element 10 is configured to serve a variety of purposes including placing or positioning the device 2 at a target location and serving as a conduit through which vacuum or suction is applied to the organ and, as described above, may also include at least one inflatable annular member inflation line 14.

The positioning element 10 may be made from a variety of materials, where the material(s) from which it is fabricated is sufficiently robust to withstand vacuum pressures ranging from about 50 to about 500 mmHg. Representative materials include, but are not limited to one or more of the following: metals or alloys thereof such as stainless steel, aluminum, titanium, and flexible and rigid plastics such as polycarbonate, polyetherimide, glass-filled polymers, or the like. In certain embodiments, the positioning element 10 may be reinforced, e.g., with a stainless steel braid or the like. The positioning element may also include a spring or the like, where such a spring or the like enables axial or vertical movements of the inflatable annular member 4 relative to the positioning element 10, and prevents kinking of the vacuum line. As such, a spring may be positioned at the distal end of the positioning element 10 such that the spring also contacts the associated cover 3, e.g., it may be positioned over the positioning element 10, inside the positioning element 10, etc. (see for example spring 132 of FIG. 5 which is positioned inside the positioning element 10). As mentioned above, the provision of a spring is applicable to all embodiments of the subject invention.

As described above, the positioning element 10 may be coupled to the inflatable annular member 4, i.e., the cover 3 of the inflatable annular member, by any suitable coupling means, where such coupling or attachment means is sufficiently robust to withstand vacuum forces, as described above, and any axial or vertical and/or lateral movements of the inflatable annular element relative to the positioning element, for example vertical and lateral movements due to a beating heart and the like. For example, see attachment means 1 of FIGS. 1 and 2. The attachment means of the subject invention may be made from a variety of materials, including plastic, metals, combinations thereof, etc.

The attachment means may be associated with the distal end of the positioning element by any suitable means including suitable chemical, mechanical, or physical means, where heat welding is of particular interest, e.g., when the attachment means is made of plastic.

The attachment means and the cover 3 of the inflatable annular member 4 may be a unitary piece of construction or may be separate components. As such, where the attachment means and the cover 3 of the inflatable annular member 4 are separate components, they may be associated using any suitable means including suitable chemical, mechanical, or physical means, where heat welding is of particular interest.

In one embodiment, the attachment means is made of a flexible material, e.g., flexible plastic such as Tygon™ tubing or the like. This configuration employing a flexible attachment means advantageously enables a sufficient degree of movement of the inflatable annular member 4 relative to the positioning device 10 to which it is associated. However, the attachment means may be made of any suitable material.

Figure 3:
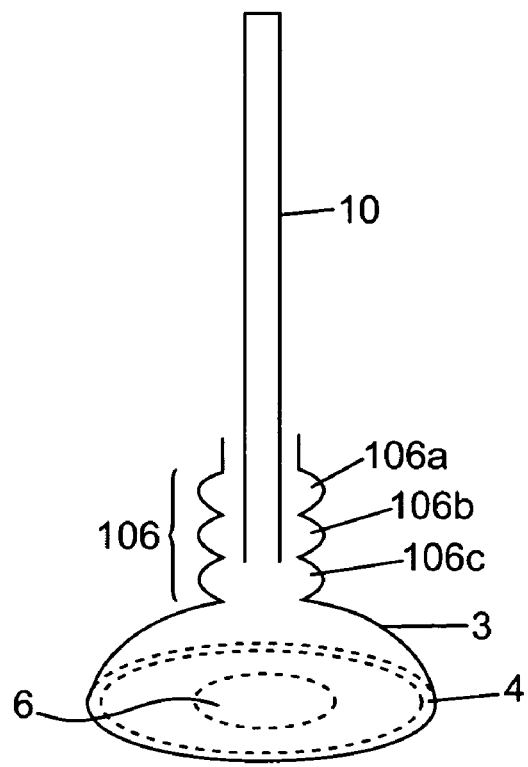
FIG. 3 shows an exemplary embodiment of a segmented attachment element.

The attachment means may take a variety of configurations. Attachment means 1 of FIGS. 1 and 2 shows one such embodiment. FIG. 3 shows another exemplary embodiment where the attachment means 106 is segmented. Accordingly, the attachment means 106 of FIG. 3 is made of a series of segments, i.e., has a bellows configuration, herein shown as three segments 106a, 106b and 106c; however, greater or fewer segments may be employed. Typically, the segments are made of a flexible plastic material such as Tygon™ tubing or the like while in other embodiments the attachment means may be made of a sufficiently rigid plastic or metal or metal alloy.

Figure 4:
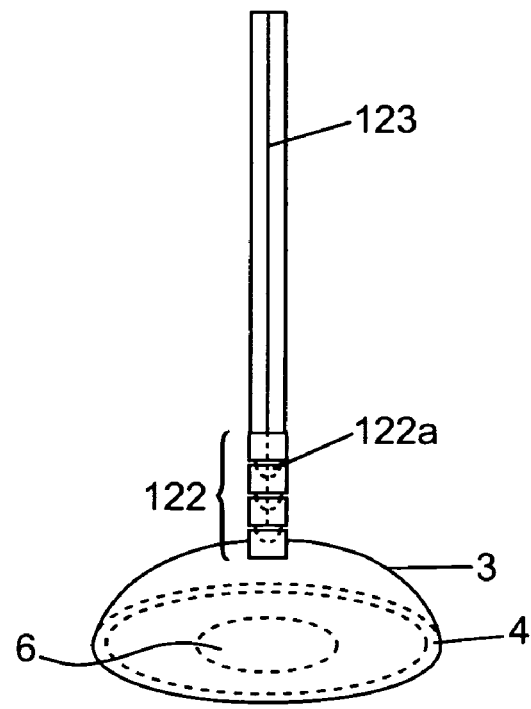
FIG. 4 shows an exemplary embodiment of a flexible linkage attachment element.

FIG. 4 shows another attachment means embodiment which enables the inflatable annular member to move vertically and horizontally, relative to the positioning element 10. Accordingly, FIG. 4 shows an attachment means which includes a flexible linkage mechanism 122 used to associate the positioning element 10 with the cover 3 of the inflatable annular member 4, where the linking mechanism may be made of a sufficiently hard plastic or metal or metal alloy. Such a linkage may be designed to have both a flexible state and a rigid state, but need not have both states. This dual state configuration, i.e., having both flexible and rigid states, is achieved by implementing a cable 123 running through a series of ball joints 122a associated with the linkage mechanism 122 and typically through the positioning element 10 as well so that linkage 122 can be changed between a flexible state and a rigid state by tightening (or un-tightening) the cable 123 using a knob mechanism with a clutch (not shown). The clutch guards against over-tightening of the assembly, and provides tactile feedback when the maximum tightening is achieved.

Figure 5:
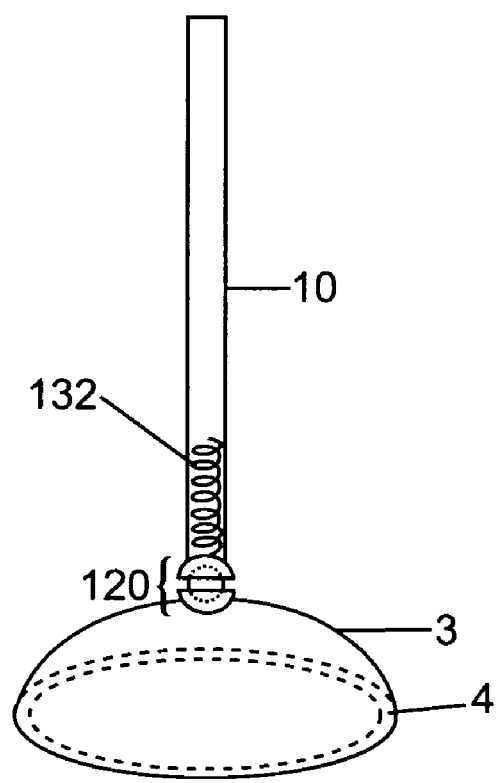
FIG. 5 shows an exemplary embodiment of an attachment means according to the present invention employing a ball and socket mechanism.

FIG. 5 shows yet another embodiment of the attachment means. FIG. 5 shows an exemplary embodiment of an attachment means employing a ball and socket mechanism 120 to associate the positioning element 10 with the cover 3 of the inflatable annular member 4. As will be apparent by those of skill in the art, such a coupling configuration enables the inflatable annular member 4 to freely rotate relative to the positioning element 10, i.e., the inflatable annular member 4 has three-dimensional rotatability. Furthermore, in certain embodiments (applicable to all attachment means embodiments), the positioning element 10 may include a spring element 132 to further enable the inflatable annular element 4 to move axially or vertically relative to the positioning element 10, as mentioned above, where such a spring is applicable to all embodiments.

Figure 6:
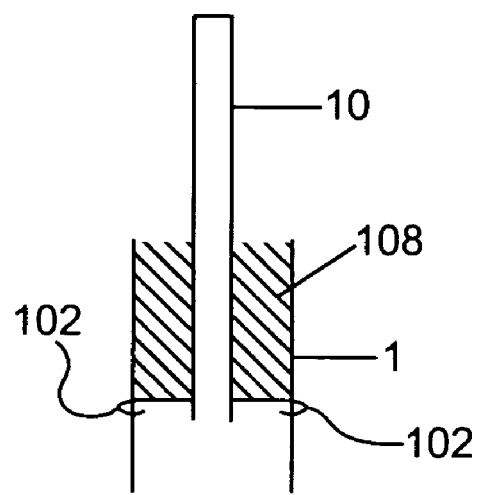
FIG. 6 shows an embodiment of the subject invention employing an adhesive and/or a grasping means to associate the positioning element with the attachment means.

As described above, the attachment means may be associated with the distal end of the positioning element by any suitable means including suitable chemical, mechanical, or physical means, where RF welding is of particular interest. FIG. 6 shows one embodiment of the subject device employing at least an adhesive to secure the attachment means to the positioning element. Accordingly, FIG. 6 shows an adhesive 108 employed to associate the positioning element 10 with an attachment means, such as attachment means 1 of FIGS. 1 and 2. In addition to, or in place of, adhesive 108, one or more grasping means such as teeth or barbs 102 positioned on the distal end of the positioning element 10 may grasp or bite into the attachment means 1. Still further, in addition to, or in place of, one or more of the above mentioned adhesive and/or teeth, the attachment means may be dimensioned or otherwise configured to intimately associate with a positioning element. For example, the attachment means may include a heat-shrinkable material which, once associated with the positioning element, is heated to a sufficient temperature and shrunk to create an intimate association.

As described above, the devices of the subject invention may be introduced to the target site through a sheath, where such a sheath may be further advanced through a suitable delivery cannula or catheter-like device. Accordingly, the subject devices may be folded or bent, i.e., resiliently deformed to be received within a sheath and, upon deployment from the sheath, assume an organ contacting or workable configuration. More specifically, the subject devices are configured to be deflatable for retention inside a sheath. After advancement out of the sheath, the devices may then be inflated. Thus, a feature of the subject devices is that they can be deflated and compressed, folded or bent, where such manipulation does not adversely affect the performance of the devices and may be done to permit delivery through an access port or the like, i.e., may be done to permit the devices to be received within a sheath for use with closed chest access procedures. However, even if a subject device is introduced via an open chest approach, it will be apparent that the subject device may still be introduced to the target site in a deflated state to facilitate placement at the target site.

Figure 7:
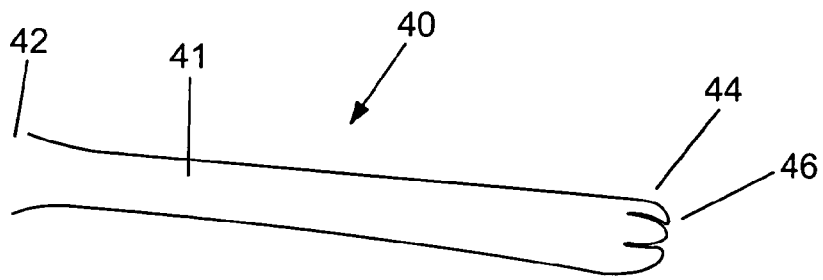
FIG. 7 shows an embodiment of a sheath according to the subject invention.
Figure 7A:
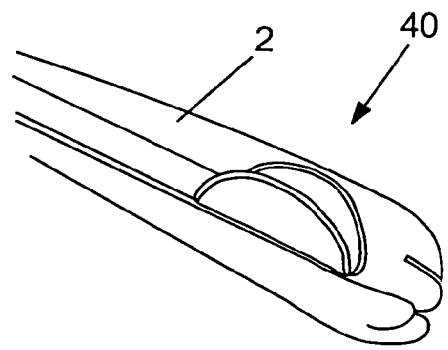
FIG. 7A shows a subject device positioned within the sheath of FIG. 8.

Any suitable sheath may be used to receive and deploy the subject devices. In general, the sheath will be biocompatible and atraumatic and dimensioned to accommodate a subject device. FIG. 7 shows an exemplary embodiment of a sheath suitable for use with the subject invention. FIG. 7 shows sheath 40 having proximal end 42, distal end 44 and a lumen or negative space 41 therethrough for accommodating a device. FIG. 7A shows the sheath 40 of FIG. 7 having a deflated subject device 2 retained therein.

Distal end 44 of sheath 40 is configured to enable atraumatic insertion of the sheath through a body cavity or catheter, as well as atraumatic deployment of a subject device from the sheath at a target site without adversely affecting the device. Accordingly, the distal end 44 of the sheath 40 may include a plurality of leaves or petals 46 to facilitate insertion of the sheath into a chest cavity and deployment of a device therefrom. In certain embodiments, the leaves 46 are biased inward to create a low profile distal end, i.e., the outer diameter at the distal end is reduced relative to the outer diameter of the body or mid portion of the sheath 40. As such, as a device is moved through the distal end 44 for deployment at a target site, the leaves 46 are urged outward by the device to allow passage of the device.

The proximal end of the sheath 40 may also be configured to enable easy loading of a subject device into the sheath. For example, in certain embodiments, the proximal end is flared to facilitate such device loading. In certain other embodiments, the sheath 40 has a slit or cut positioned along its longitudinal axis, through which a device may be loaded (see for example FIG. 7A) for insertion or removal from a body cavity. The subject devices may be supplied pre-loaded in a sheath or may be supplied separately and loaded prior to use.

The subject sheath 40 can be made from a variety of biocompatible materials, where such materials include, but are not limited to, plastics such as polypropylene, Teflon, low density polyethylene, metals and metal alloys such as titanium, stainless steel, Nitinol or other shape memory alloys, etc.

Typically, the sheath 40 is configured to intimately retain a subject device in its deflated state. Accordingly, the outer diameter of the sheath 40, exclusive of the distal end if inwardly biased leaves are present, usually ranges from about 3 to about 25 mm, usually from about 5 to about 12 mm. In those embodiments having inwardly biased leaves or petals at the distal end, the outer diameter of such an inwardly biased area usually ranges from about 3 to about 25 mm, usually from about 5 mm to about 12 mm. In those embodiments having a flared proximal end, the outer diameter of such a flared area typically ranges from about 10 mm to about 50 mm, usually from about 10 to about 24 mm. The length of the sheath will of course vary depending on a variety of factors, including, but not limited to, the type of procedure performed, i.e., open or closed chest, the organ of interest, i.e., the particular organ and the position thereof in the body cavity, and the like. However, by way of example and not limitation, when used to deploy a subject device using a closed chest procedure, e.g., through a port positioned in the chest wall, for manipulating and/or positioning an adult, human beating heart, the length of the sheath 40 will typically range from about 4 to about 12 inches, usually from about 6 to about 8 inches.

The subject device may be maintained in a particular position by being secured to a stationary or fixed object such as a surgical table, surgical retractor, e.g., a sternal retractor, a portion of the patient's skeletal system, e.g., the sternum, the floor, the ceiling, and the like. As such, the subject device may itself be secured to a stationary or fixed object, i.e., the positioning arm of the subject device may be secured, e.g., with a mount or the subject device may be associate with a means for attachment to a stationary or fixed object. For example, the subject invention may also include a securing means, where suitable securing means typically includes at least an arm, either flexible or rigid, a mount for attachment to a stationary object, as described above, and a means for associating the positioning element of the subject device with the securing means. Securing means suitable for use with the subject invention include, but are not limited to, those described in U.S. Pat. Nos. 6,331,158; 6,338,712; 6,361,493; 6,375,611; 6,390,976; 6,506,149; 6,626,830; 6,652,454; and 6,656,113, each of which is incorporated herein, in its entirety, by reference thereto.

Methods

As summarized above, methods are also provided for manipulating and positioning an organ. The subject methods may be used to manipulate and position a wide variety of organs including, but not limited to, hearts, e.g., hearts such as beating hearts, stomachs, gall bladders, livers, spleens, intestines, etc. The subject methods may also be used with both open and closed chest procedures such as sternotomies, mini-sternotomies, thoracotomies or mini-thoracotomies, or through a port provided within the chest cavity of the patient, e.g., between the ribs or in a subxyphoid area, with or without the visual assistance of an thoracoscope. Furthermore, the subject methods are suitable for use with both off pump and on pump procedures, i.e., are suitable for use during a cardiopulmonary bypass procedure (i.e., a stopped heart procedure where the patient's heart is stopped and certain physiological functions are provided by a cardiopulmonary bypass machine) or during a procedure wherein the patient is not on cardiopulmonary bypass (i.e., a beating heart procedure where the patient's heart continues to beat during the procedure). In further describing the subject methods, an exemplary method with respect to manipulating and positioning a beating heart will be used. However, it is to be understood that this is for exemplary purposes only and is in no way meant to limit the scope of the invention, as the subject invention may be used for a variety of procedures, as described above. It is also important to note that the order of the below described method steps may be altered or changed, depending on the particular clinical needs of the patient, surgeon, etc. For example, a subject device may be inflated before insertion into a body cavity, after insertion into a body cavity, before organ contact, after organ contact, etc., as will be obvious to those of skill in the art.

Thus, the subject methods may be used to manipulate a beating heart to provide access to one or more arteries positioned on the lateral or posterior aspects of the heart for a coronary artery bypass graft procedure. The subject methods and devices are useful for moving the heart around in a closed chest, to provide access and visualization to desired regions on the heart. For example, it may be necessary to bypass multiple coronary arteries, including the circumflex artery (CxA) on the left lateral aspect of the heart, the right coronary artery (RCA) on the right lateral aspect of the heart, and the posterior descending artery (PDA) on the back side of the heart, where access to such arteries is difficult and where manipulating the heart will increase or facilitate accessibility thereto.

Thus, the first step in the subject methods is to provide a device capable of manipulating and positioning the heart. In other words, a device which is configured to manipulate and position the heart without any significant adverse hemodynamic consequence (i.e., is hemodynamically insignificant) and which may also be configured to be advanced to the heart through a closed chest, i.e., through a port positioned in the chest wall, or the like, is provided, such as a subject device as described above. The device may be provided in an inflated, organ contacting state, i.e., a working configuration, or in a deflated state and may be provided within a sheath such as a sheath as described above. Once the provision of a suitable device has been met, the device is then delivered or brought to the target site, e.g., the area of the heart, usually the area of the apex of the heart.

As mentioned above, the device may be introduced to the site through an open or partially opened chest, (i.e., through an open or partially opened sternotomy, thoracotomy or sub-xyphoid approach) or may be introduced through a port, i.e., an access port or stab wound, typically positioned intercostally, i.e., between adjacent ribs. In those embodiments where the device is introduced via a port or other entry means not capable of accommodating a fully inflated subject device, the device is typically retained in a suitable sheath such as the sheath described above, for easy introduction and delivery. As such, the device is resiliently deformed into a deflated state and loaded into a sheath (see FIG. 7A). In other words, the device is deflated and compressed, folded and/or bent to fit inside the sheath for port access introduction, where it is then delivered to the target site, advanced out of the sheath and inflated.

Regardless of when the device is inflated or how it is brought to the target site, the device may be inflated using any suitable substance or agent. In many embodiments of the subject device, the inflatable annular member is inflated with a gas such as oxygen, nitrogen, carbon dioxide and inert gases such as helium, neon, argon, and the like. However, the inflatable annular member may also be inflated with substances or agents other than gas, for example a fluidic substance such as saline, water, contrast solution, etc., or any combination thereof may be employed to inflate the annular member.

Figure 8:
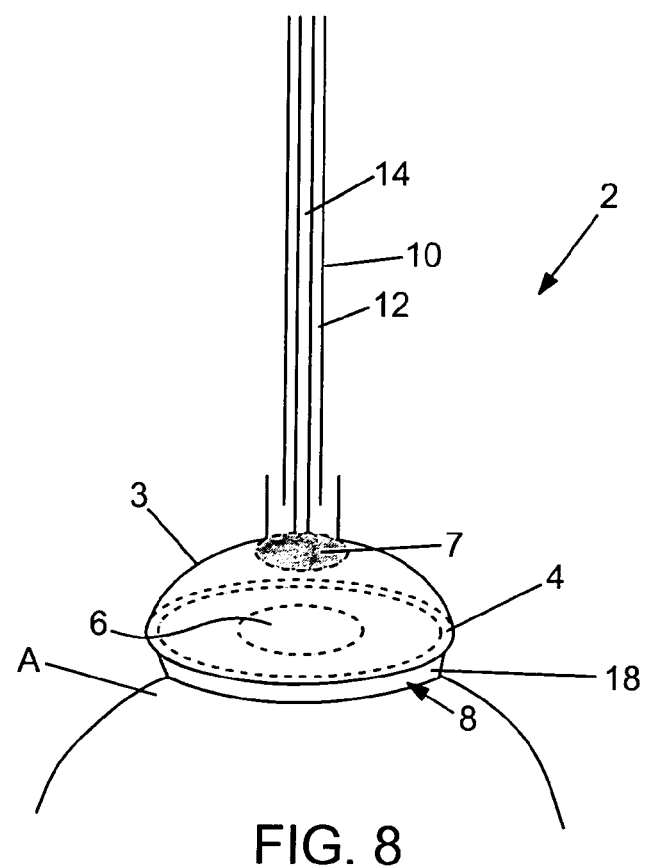
FIG. 8 shows an exemplary device according to the subject invention contacting an apex of a beating heart

Once inflated, the device is contacted with the organ of interest, e.g., a beating heart, usually the apex of the beating heart. In many embodiments, the soft, compliant material associated with the organ contacting side of the device, as described above, is contacted with the apex. FIG. 8 shows an exemplary device according to the subject invention such as device 2 of FIG. 1 contacting an apex A of a beating heart.

Once contacted, a vacuum or suction is applied such that the organ, e.g., the apex A of a beating heart, is further engaged with the device 2. In other words, the organ contacting surface 8 contacts the organ to conformingly engage the organ. The amount of vacuum applied will vary depending on a variety of factors including, but not limited to, the particular organ being manipulated, i.e., the size and shape of the organ of interest, and the like. Typically, where the organ of interest is a beating, adult human heart, about 100 mmHg to about 400 mmHg of vacuum is applied, usually about 200 mmHg to about 300 mmHg is applied and more usually about 250 mmHg to about 300 mmHg is applied.

Once the vacuum is applied, a seal between the organ and the device is accomplished due to the applied suction force. Furthermore, the vacuum is usually distributed or diffused over a large area, for example diffused over the organ contacting area or interface, e.g., over the soft, compliant material 18 of the organ contacting area 8 and/or also over the central opening 6 of the device if a vacuum distribution element 7 is present, as described above.

Once a sufficient seal has been established between the organ and the device, the device is manipulated, e.g., to provide access to arteries or areas of interest otherwise obscured by the organ. In other words, the organ may be lifted, tilted, rotated, etc., to enable the surgeon to access areas of the organ or area(s) usually inaccessible or difficult to access, i.e., usually obscured by the organ such as the lateral and/or backside of the organ. Accordingly, the organ, e.g., a beating heart, is physically translated from its natural resting place to a location better suited to surgical access, and then the organ is held in the latter location during surgery without compressing (or otherwise deforming) the organ, i.e., without adversely compressing the heart or great vessels, in such a way that hemodynamic function is compromised or aversely affected.

The organ may be maintained in such a manipulated position by affixing the device to a stationery or fixed object such as a surgical table, surgical retractor, e.g., a sternal retractor, a portion of the patient's skeletal system, e.g., the sternum, the floor, the ceiling, and the like, where such a fixation may be accomplished by affixing the positioning element of the device itself to an object or by securing the positioning element to a suitable securing means, as described above, where the securing means is then affixed to an object. Still further, the device may be held in place by the surgeon or the surgeon's assistant, i.e., the positioning element of the device may be held.

The surgeon next performs the appropriate procedure on or involving the manipulated and positioned organ, or a newly accessible area around the manipulated and positioned organ. For example, in those embodiments where a heart is manipulated to facilitate a CABG procedure, once manipulated and positioned to expose the blocked arteries, the surgeon may perform one or more necessary arterial bypasses of the now accessible, blocked arteries. In certain embodiments of the subject methods, visualization of the site is achieved by endoscopic or thoracoscopic means. For example, where the procedure is performed through one or more ports positioned in the chest wall, an endoscope or thoracoscope may also be inserted through a port (i.e., through the same or different port than the one used to introduce the device) to facilitate visualization of the site. During the procedure, particularly a beating heart CABG procedure, the device is able to move to accommodate the natural rhythms or movements of the organ, e.g., a beating heart. In other words, the device has sufficient axial or vertical and lateral movement to accommodate a beating heart.

Following the procedure, the organ is then returned to its original position and disengaged from the device. As such, the organ is gently returned to its natural orientation. The vacuum to the device is then turned off to break the seal between the organ and the device and the device is removed from the body cavity. Depending on the technique used to introduce the device into the body, the device may be first deflated and then removed or may be removed in its inflated state, e.g., where the device can be removed through a full sternotomy or the like. In certain embodiments of the subject methods where the device had been retained inside a sheath and introduced through an access port, the device may be deflated, and then removed from the body cavity through an access port. The access site, i.e., the sternotomy, thoracotomy, access port, or the like, is then closed using conventional methods and the patient is prepared for post-op, as is known in the art, e.g., one or more drainage tubes may be placed, the patient may be disengaged from CPB if used, etc.

Kits

Also provided are kits for manipulating and positioning an organ, e.g., a beating heart. The subject kits include at least a subject device, and oftentimes a plurality of such devices, where the devices may be the same or different, e.g., may be the same or different sizes and/or shapes. The kits may further include one or more sheath for delivering the subject device(s) to a target site and may also include one or more securing means for attaching the subject device(s) to a stationary or fixed object. In certain embodiments of the subject kits, one or more regulators are included for regulating the flow of a vacuum source to an organ. Finally, the kits may further include instructions for manipulating and positioning an organ, e.g., instruction for using the subject devices for manipulating and positioning an organ. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides an easy and effective way to manipulate and position an organ, e.g., a beating heart. The above described invention provides a number of advantages, including ease of use, hemodynamic insignificance, clinically significant range of motion (i.e., sufficient lateral and axial movement), the ability to be used with a variety of organs and use with both open and closed chest procedures, i.e., may be delivered via sheath to a site. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the resent invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for manipulating and positioning an organ, said device comprising:
   an inflatable member having an opening passing therethrough and an organ contacting surface;
   a positioning element comprising a lumen passing through at least a portion thereof, said positioning element connected to said inflatable member and sealing one end of said opening, wherein an opposite end of said opening remains open and passes through said organ contacting surface, said lumen configured to be coupled to a vacuum source and fluidly communicate with said opening through said inflatable member, wherein said positioning element is configured to position said inflatable member and deliver negative pressure to a surface of the organ via said lumen and said opening, when said organ contacting surface contacts the organ.

2. The device according to claim 1, wherein the organ is a beating heart.

3. The device according to claim 1, wherein one or more seams of said inflatable member is positioned on the interior of said inflatable member.

4. The device according to claim 1, wherein the organ contacting surface comprises an atraumatic, compliant material.

5. The device according to claim 4, wherein said atraumatic, compliant material is configured to conform to, and diffuse suction exerted on, the organ.

6. The device according to claim 1, further comprising a vacuum distribution element fluidly interconnecting said lumen and said opening, said vacuum distribution element being configured to diffuse the negative pressure applied to the surface of the organ.

7. The device of claim 6, wherein said vacuum distribution element is selected from the group consisting of foam, gel, fabric, gauze, and material of the type conventionally used in neuro sponges.

8. The device of claim 1, further comprising an attachment element interconnecting said inflatable member and said positioning element, wherein said attachment element fluidly seals a connection of said lumen with said opening and allows limited freedom of movement of said inflatable member with respect to said positioning element, such that when said inflatable member is engaged with the surface of the organ, normal movements of the organ are permitted by movement of said inflatable member with respect to said positioning element.

9. The device of claim 8, wherein said attachment element comprises a flexible plastic.

10. The device of claim 8, wherein said attachment element comprises a series of segments.

11. The device of claim 8, wherein said attachment element comprises a flexible linkage mechanism.

12. The device of claim 8, wherein said attachment element comprises a ball and socket mechanism.

13. The device of claim 8, wherein said attachment element is configured to allow vertical and lateral movement of said inflatable member, when engaged with the organ, where the organ is a beating heart, and when said positioning element is held relatively stationary, so as not to reduce negative effects on hemodynamics of the beating heart.

14. The device of claim 1, wherein said positioning element further comprises a spring to enable axial movement of said inflatable member relative to said positioning element.

15. The device of claim 1, further comprising an inflation line configured to be connected with a source of fluid, and fluidly connected to said inflatable member, said inflation line being independent of a fluid pathway established by said lumen.

16. The device of claim 15, wherein inflatable member is resiliently deformable to a deflated configuration by application of negative pressure through said inflation line.

17. The device of claim 15, wherein said inflatable member is inflatable by delivery of a pressurized fluid through said inflation line.

18. The device according to claim 16, further comprising a sheath configured to receive said inflatable member in said deflated configuration.

19. The device of claim 1, further comprising a securing means for securing said device to a stationary object.

20. A method of manipulating and positioning an organ, said method comprising:
introducing a deflated member of a device into a body cavity;
inflating the member to an inflated configuration;
contacting the organ with the inflated member;
applying a vacuum to the organ through an opening that passes through an organ contacting surface of the inflated member, while maintaining the inflated member in the inflated configuration, to create an intimate engagement between the organ and the inflated member; and
moving the inflated member, to manipulate or position the organ.

21. The method of claim 20, wherein the deflated member is introduced into the body cavity through an opening created by one of a sternotomy, mini-sternotomy, thoracotomy, mini-thoracotomy and a port.

22. The method of claim 20, wherein the deflated member is encased in a sheath during said introducing.

23. The method of claim 20, wherein the pressurized fluid is selected from one of the group consisting of gas, saline, water, contrast solution, and combinations thereof.

24. The method of claim 20, wherein the organ is a beating heart.

25. The method of claim 20, further comprising diffusing a flow of the vacuum through said opening to the organ.

26. The method according to claim 20, further comprising securing said device to a stationary object.

27. The method according to claim 20, further comprising performing a coronary artery bypass procedure on the organ.

28. The method according to claim 20, wherein said device is manipulated and positioned absent clinically relevant hemodynamic instability.

29. A kit for manipulating and positioning an organ, said kit comprising:
(a) at least one device according to claim 1; and
(b) instructions for using said device to manipulate and position the organ.

30. The kit according to claim 29, comprising a plurality of devices.

31. The kit according to claim 29, further comprising at least one sheath for delivering said device into a body cavity.

32. The kit according to claim 29, further comprising at least one securing means for securing said device to a stationary object.

33. The kit according to claim 29, further comprising at least one regulator for regulating a flow of vacuum.

34. A device for manipulating and positioning an organ, said device comprising:
an inflatable member having an opening passing therethrough and an organ contacting portion surrounding a distal end of said opening, wherein said opening passes through said organ contacting portion;
a first lumen connected to a proximal end of said opening and forming a fluid seal with said proximal end, said first lumen configured to deliver negative pressure through said opening;
a second lumen fluidly connected to said inflatable member and not fluidly connected with said opening; and
a positioning element connected to said inflatable member.

35. The device of claim 34, further comprising an attachment element interconnecting said inflatable member and said positioning element, wherein said attachment element allows limited freedom of movement of said inflatable member with respect to said positioning element, such that when said inflatable member is engaged with the surface of the organ, normal movements of the organ are permitted by movement of said inflatable member with respect to said positioning element.

36. The device of claim 34, further comprising a vacuum distribution element fluidly interconnecting said lumen and said opening, said vacuum distribution element being configured to diffuse the negative pressure applied to a surface of the organ through said distal end of said opening.

37. A device for manipulating and positioning an organ, said device comprising:
an inflatable member having an opening passing therethrough and an organ contacting surface;
a positioning element comprising a lumen passing through at least a portion thereof, said positioning element connected to said inflatable member and sealing one end of said opening, said lumen configured to be coupled to a vacuum source and fluidly communicate with said opening through said inflatable member, wherein said positioning element is configured to position said inflatable member and deliver negative pressure to a surface of the organ via said lumen and said opening, when said organ contacting surface contacts the organ; and an attachment element interconnecting said inflatable member and said positioning element, wherein said attachment element fluidly seals a connection of said lumen with said opening and allows limited freedom of movement of said inflatable member with respect to said positioning element, such that when said inflatable member is engaged with the surface of the organ, normal movements of the organ are permitted by movement of said inflatable member with respect to said positioning element;

wherein said attachment element comprises a flexible linkage mechanism.

38. A device for manipulating and positioning an organ, said device comprising:

an inflatable member having an opening passing therethrough and an organ contacting surface;

a positioning element comprising a lumen passing through at least a portion thereof, said positioning element connected to said inflatable member and sealing one end of said opening, said lumen configured to be coupled to a vacuum source and fluidly communicate with said opening through said inflatable member, wherein said positioning element is configured to position said inflatable member and deliver negative pressure to a surface of the organ via said lumen and said opening, when said organ contacting surface contacts the organ; and an attachment element interconnecting said inflatable member and said positioning element, wherein said attachment element fluidly seals a connection of said lumen with said opening and allows limited freedom of movement of said inflatable member with respect to said positioning element, such that when said inflatable member is engaged with the surface of the organ, normal movements of the organ are permitted by movement of said inflatable member with respect to said positioning element;

wherein said attachment element comprises a ball and socket mechanism.

39. A device for manipulating and positioning an organ, said device comprising:

an inflatable member having an opening passing therethrough and an organ contacting surface;

a positioning element comprising a lumen passing through at least a portion thereof, said positioning element connected to said inflatable member and sealing one end of said opening, said lumen configured to be coupled to a vacuum source and fluidly conmunicate with said opening through said inflatable member, wherein said positioning element is configured to position said inflatable member and deliver negative pressure to a surface of the organ via said lumen and said opening, when said organ contacting surface contacts the organ; and an attachment element interconnecting said inflatable member and said positioning element, wherein said attachment element fluidly seals a connection of said lumen with said opening and allows limited freedom of movement of said inflatable member with respect to said positioning element, such that when said inflatable member is engaged with the surface of the organ, normal movements of the organ are permitted by movement of said inflatable member with respect to said positioning element;

wherein said attachment element is configured to allow vertical and lateral movement of said inflatable member, when engaged with the organ, where the organ is a beating heart, and when said positioning element is held relatively stationary, so as not to reduce negative effects on hemodynamics of the beating heart.

* * * * *

UNITED STATES PATENT AND TRADEMARK OFFICE
CERTIFICATE OF CORRECTION

PATENT NO. : 7,179,224 B2  
APPLICATION NO. : 10/749061  
DATED : February 20, 2007  
INVENTOR(S) : Willis It is certified that error appears in the above-identified patent and that said Letters Patent is hereby corrected as shown below:

Column 1, line 21, please delete "stemotomy" and insert therefore --sternotomy--
Column 1, line 21, please delete "mini-stemotomy" and insert therefore --mini-sternotomy--
Column 1, line 32, please delete "stemotomy" and insert therefore --sternotomy--
Column 1, line 40, please delete "stemotomy" and insert therefore --sternotomy--
Column 1, line 44, please delete "stemotomy" and insert therefore --sternotomy--
Column 1, line 45, please delete "stemotomy" and insert therefore --sternotomy--
Column 3, line 9, please delete "stemotomy" and insert therefore --sternotomy--
Column 3, line 9, please delete "mini-stemotomy" and insert therefore --mini-sternotomy--
Column 4, line 22, please delete "stemotomies" and insert therefore --sternotomies--
Column 4, line 22, please delete "mini-stemotomies" and insert therefore --mini-sternotomies--
Column 5, line 32, please delete "stemotomies" and insert therefore --sternotomies--
Column 5, line 33 please delete "mini-stemotomies" and insert therefore --mini-sternotomies--
Column 13, line 5, please delete "stemotomies" and insert therefore --sternotomies--
Column 13, line 62, please delete "stemotomy" and insert therefore --sternotomy--
Column 17, line 61, please delete "mini-stemotomy" and insert therefore --mini-sternotomy--

Signed and Sealed this

Twenty-third Day of September, 2008

JON W. DUDAS  
*Director of the United States Patent and Trademark Office*